(12) United States Patent
Mafra-Neto et al.

(10) Patent No.: US 9,693,561 B2
(45) Date of Patent: Jul. 4, 2017

(54) COMPOSITIONS AND METHODS FOR ATTRACTING MOSQUITOES AND REPELLING SAND FLIES

(71) Applicant: ISCA Technologies, Inc., Riveside, CA (US)

(72) Inventors: Agenor Mafra-Neto, Riverside, CA (US); Rodrigo Oliveira Da Silva, Riverside, CA (US); Carmem R. Bernardi, Riverside, CA (US)

(73) Assignee: ISCA Technologies, Inc., Riverside, CA (US)

( * ) Notice: Subject to any disclaimer, the term of this patent is extended or adjusted under 35 U.S.C. 154(b) by 0 days.

(21) Appl. No.: 14/938,696

(22) Filed: Nov. 11, 2015

(65) Prior Publication Data

US 2016/0128327 A1    May 12, 2016

Related U.S. Application Data

(60) Provisional application No. 62/078,039, filed on Nov. 11, 2014.

(51) Int. Cl.
| | |
|---|---|
| *A01N 49/00* | (2006.01) |
| *A01N 27/00* | (2006.01) |
| *A01N 31/02* | (2006.01) |
| *A01N 31/08* | (2006.01) |
| *A01N 35/02* | (2006.01) |
| *A01N 65/00* | (2009.01) |
| *A01N 25/00* | (2006.01) |

(52) U.S. Cl.
CPC ........... *A01N 49/00* (2013.01); *A01N 25/006* (2013.01)

(58) Field of Classification Search
None
See application file for complete search history.

(56) References Cited

U.S. PATENT DOCUMENTS

| | | |
|---|---|---|
| 2004/0242699 A1 | 12/2004 | Askham et al. |
| 2006/0189690 A1 | 8/2006 | Dunham et al. |
| 2007/0269404 A1 | 11/2007 | Simchoni-Barak et al. |
| 2008/0254083 A1 | 10/2008 | Mafra-Neto |
| 2010/0216730 A1 | 8/2010 | Boucher, Jr. et al. |
| 2013/0104445 A1 | 5/2013 | Schneidmiller et al. |
| 2013/0158130 A1 | 6/2013 | Heuer et al. |

OTHER PUBLICATIONS

Search report & Written Opinion of PCT/US15/60214, Authorized Officer: Lee W. Young, Mar. 2, 2016.

*Primary Examiner* — Aradhana Sasan
(74) *Attorney, Agent, or Firm* — Benjamin Diederich; Law Office of Benjamin Diederich

(57) ABSTRACT

Compositions and methods for affecting dipteran hematophagous parasites. The compositions contain at least one dipteran semiochemical and at least one phagostimulant. The compositions may further include a pesticide. The semiochemical may be a floral attractant and the phagostimulants may be sugar-based. The compositions may be useful in attracting mosquitoes and/or repelling sand flies.

21 Claims, No Drawings

COMPOSITIONS AND METHODS FOR ATTRACTING MOSQUITOES AND REPELLING SAND FLIES

CROSS-REFERENCE TO RELATED APPLICATIONS

This application claims the benefit of U.S. Provisional Application No. 62/078,039, filed on Nov. 11, 2014, the teachings of which are expressly incorporated by reference.

STATEMENT RE: FEDERALLY SPONSORED RESEARCH/DEVELOPMENT

Not Applicable

BACKGROUND

1. Field of the Invention

The present invention relates to products, systems, and methods for controlling adult populations of blood-feeding insects, both nuisance pests and vectors of disease. More specifically, this invention relates to methods and systems for attracting multiple species of mosquitoes, for purposes of both population control and monitoring; and for repelling New and Old World sand flies (vectors of leishmaniasis) through the use of a novel combination of floral plant volatile semiochemicals with potent and varied behavioral effects. This semiochemical formulation can be employed in a broad range of means, including a monolithic lure and attractant-impregnated adhesive to be deployed in monitoring traps, and a liquid formulation that can be blended with insecticide to create an attract and kill product amenable to spray application. It is also deployable in larger quantities in strategically placed, self-contained bait stations.

2. Background of the Invention

Insects of all species rely predominately on chemicals detected in their environment for virtually every critical aspect of their lives, from females' selection of appropriate sites upon which to deposit their eggs, location of desirable habitats and food sources and the avoidance of undesirable ones, to the finding and selection of a mate. These behavior-modifying chemicals, known collectively as semiochemicals, have often been used in attempts to manage or suppress insect pest populations through a wide variety of methods, such as mating disruption (artificial treatment of a vulnerable field or environment with synthetic sex pheromone in such a way that the male insect is unable to locate a male within that field); the placement of an attractant in a monitoring trap or as part of a mass trapping program; repellency, to drive insects away from susceptible host organisms; and attract and kill (A&K), in which an attractant is applied in combination with a killing agent, typically a small quantity of insecticide, to draw insects to a defined location and kill them before they can either reproduce or cause any damage or disease to host organisms.

The pests targeted by the present invention, dipteran hematophagous parasites (those that feed on the blood of humans and animals and in so doing transmit a broad range of blood-borne pathogens), include some of the most harmful insects to the health and prosperity of human populations, both in the U.S. and abroad, that the world has ever known. Mosquitoes transmit some of the most devastating human diseases around the world, such as malaria, arbovirus fevers such as dengue, yellow fever, chikungunya and West Nile virus, and filarial diseases, such as elephantiasis and river blindness among others. Vector-borne diseases transmitted by insects are increasing in prevalence worldwide, and it is likely this trend will only increase in importance as climate patterns change in the future. According to the American Mosquito Control Association, over one million people die from mosquito-borne diseases each year. West Nile virus is currently the mosquito-borne disease (MBD) of greatest concern in the U.S., with over 30,000 human cases reported to the CDC since the disease was first detected in 1999. Historically, several other mosquito-borne diseases, including malaria, yellow fever, and dengue fever, were common killers in the United States. Persistent mosquito control efforts in this country and other industrialized nations have protected their citizens from mosquito-borne illnesses for decades. Although these efforts have been successful in keeping many of us from contracting these illnesses, recent outbreaks of dengue fever, eastern equine encephalitis and the constant threat of West Nile virus are a sobering reminder of the constant necessity for effective, accurate mosquito control and monitoring techniques.

Sand flies also exert harmful impacts on people all over the globe, especially in under-developed regions, as vectors of leishmaniasis, caused by infection with *Leishmania* parasites. According to estimates by the U.S. Centers for Disease Control and the World Health Organization, leishmaniasis is found in over 90 countries, putting over 310 million people at risk. Approximately 300,000 cases of visceral leishmaniasis, the more severe form of the disease, are reported each year, resulting in over 20,000 deaths. While leishmaniasis is curable with proper treatment, most cases occur in impoverished regions, where access to health care is often limited. No vaccines are available to prevent *Leishmania* infection. The best method of preventing the disease is to prevent contact between sand flies and their hosts, making effective, low-cost control technologies a major priority in affected areas.

In addition to the impacts biting dipterans have through their capacity to transmit disease, their blood-feeding behavior itself exerts harmful effects on productivity and quality of life for the people and animals they feed upon, particularly for outdoor workers, residents of rural or remote communities, and livestock species. Animals suffering from attacks by large numbers of mosquitoes—under these circumstances, ruminants like cattle and sheep can lose as much as 300 mL of blood in a single day—often do not feed properly, grouping together and attempting to fend off mosquitoes rather than grazing, resulting in decreased weight gains and reduced milk production in dairy cattle. There is a scarcity of recent data attempting to quantify these losses, but older reports estimate economic losses of up to $61 million in a year as a result of mosquito feeding on livestock.

Nuisance biting by hematophagous dipterans also negatively impacts human productivity and prosperity. Aside from the economic opportunity lost if an individual contracts a vector-borne illness on the job, productivity among outdoor workers has been shown to plummet when they are forced to share their work environments with large numbers of mosquitoes. In some cases, agricultural employees may refuse to work where mosquito populations are high. Nuisance mosquitoes may also decrease property values; this is particularly evident in the southeastern U.S. Before the implementation of organized mosquito control efforts in the state of Florida, coastal communities suffered such severe mosquito infestations that they were actually forced to close down during the summer months. Better mosquito control practices have not only fostered better quality of life in these communities, but have also enabled further development of coastal regions, leading to an influx of tourism. There has been found to be a correlation between declining populations of *Aedes taceniorhynchus*, the saltmarsh mosquito, and increased tourist expenditures.

In light of these impacts, it is little surprise that there is an ever-increasing demand for effective vector control products. The total market size for mosquito adulticides (pesticide products specifically targeting adult insects) alone is estimated at $4.8 billion. More than 352 million acres are managed for vector control by approximately 1800 mosquito control districts and municipalities in the U.S. at an average cost of around $5/acre/day, a market size of approximately $4 billion per year. This is an expanding market, in the U.S. and globally, and is currently dominated by conventional chemical insecticides, particularly by broad-spectrum pyrethroid and organophosphate sprays. Though these types of products have produced good results in the past, delivering a high degree of mortality against multiple species of blood-feeding dipterans, they possess a number of disadvantages that make them an unsustainable pest management solution over the long term, both environmentally and practically. First, as most conventional insecticides kill by contact, they must be blanket sprayed over all surfaces where mosquitoes are thought to be present in order to provide effective population control. This has led to a high degree of public concern regarding the negative effects these chemicals may have on the environment (persistence in the soil, contamination of water supply, spray drift, etc.) and on non-target species (i.e., people, beneficial insects such as pollinators and natural enemies, livestock and companion animals), especially when they are applied near human habitations.

Secondly, as relatively simple chemical toxicants with only a single mode of action, all conventional insecticides developed thus far share a common weakness: the potential for the population of the target insect to become less susceptible—and eventually, all but invulnerable—to them over time. This loss of sensitivity to a particular toxin, called resistance, is more likely to occur when that toxin is applied over a wide area, against multiple consecutive generations of the target insect, and begins when certain individuals within the population, having genes that make them more resilient to the chemical being used, survive exposure to it long enough to produce viable offspring. These offspring then carry these genes on to the next generation, creating the beginnings of a population that is resistant to the toxin.

Another critical component of an effective system of management for biting dipterans is an accurate and timely method of population monitoring. Current monitoring traps tend to rely on a certain class of semiochemicals in order to attract mosquitoes and other blood-feeding insects: host scent cues naturally produced by vertebrates, such as carbon dioxide (CO2), which these insects use to orient toward a potential source for a blood meal. However, traps relying on CO2 as a lure for dipterans can be extremely expensive ($300-41400 for the initial purchase), cumbersome, and challenging to maintain, requiring a constant supply of electrical or battery power and frequent replenishing of the CO2 source in order to function effectively. They are also inherently limited in their capacity to attract the target insects: CO2 and other attractants designed to mimic the scent profile of a vertebrate host are only attractive to female dipterans seeking a blood meal. Scientists and vector control researchers have long focused on female blood feeding and methods of breaking transmission at this stage, but we believe this is an improper area of emphasis. Blood feeding behavior, despite its importance to mosquitoes' impacts as disease vectors, is actually a comparatively rare event in the insect's life cycle. Female mosquitoes do not require a blood meal to nourish themselves, only to complete development of their eggs, and so are only required to pursue this food source two or three times during their lives, while males do not blood feed at all. A trapping program or an A&K strategy using CO2 or any other vertebrate host cue would therefore only have one or two opportunities to eliminate a mosquito before it becomes capable of transmitting a pathogen (a minimum of two blood meals is required for transmission to occur, one to acquire the pathogen from an infected individual, and one to introduce it to an uninfected individual).

As such, we have designed the current invention to exploit another aspect of hematophagous insect behavior, common to all mosquitoes, both nuisance and vector species, regardless of gender, age, feeding preference, or physiological status: their reliance on sugar solutions to fuel their metabolism. Sugar-based food sources, mainly acquired from flowers and extra-floral nectaries, are absolutely essential in order to sustain the highly active, highly mobile lifestyle that enables mosquitoes and sand flies to survive and reproduce. As such, mosquitoes seek sugar meals on an almost daily basis throughout their lives, relying on floral-produced scent plumes to guide them to appropriate sources of nectar and plant juices, from the time they emerge as adults to the time they die. A female mosquito will engage in this sugar-seeking behavior multiple times before ever pursuing a vertebrate host for blood feeding; she may take from eight to 12 sugar meals prior to her first blood meal, making her far more vulnerable to a floral or sugar-based attractant than to one intended to mimic the scent of a potential blood meal source. A floral plant volatile-based attractant, therefore, would have as many as 10 more opportunities to capture or kill a dipteran vector before it can transmit disease than an attractant meant to manipulate blood-feeding behavior.

Our invention, called Vectrax, is designed as a highly potent and versatile blend of floral attractants and sugar-based phagostimulants that will act as an effective lure for all species of mosquitoes, of either gender, of all physiological states. This invention can be utilized in a wide variety of methods. Vectrax can be deployed alone to substantially improve monitoring efforts for vector mosquitoes of both established and emerging MBDs in the U.S., or blended with small quantities of insecticide to create an attract and kill (A&K) formulation.

For monitoring purposes, this attractant blend could be deployed as a long-lasting monolithic lure, to be placed in virtually any type of trap, or it could be blended directly into the adhesive for a sticky trap. Neither of these trap-lure systems would require a source of power or a CO2 source in order to function, drastically reducing the effort and cost required to deploy and maintain the trap. This enhanced monitoring capacity could help not only to improve strategic timing and location of mosquito control efforts (i.e., identification of key mosquito reproductive sites, targeting of high populations by insecticide sprays), but also improve surveillance of mosquito-borne illnesses, both those already established, and those threatening to invade from foreign regions. Current methods of surveillance of these diseases are to a great extent reliant on case reports of both infected people and animals—a relatively slow and ineffective indicator, at least in terms of informing vector management decisions: mosquitoes responsible for a given case of infection with a mosquito-borne pathogen are likely to be long gone from the area where transmission occurred by the time the case is reported. While mosquitoes collected in CO2 monitoring traps have also been used as a means to track vector-transmitted illnesses, this method of surveillance can also be impractical if the prevalence of the pathogen is low, such as would be the case with a newly introduced pathogen. In such a situation, so few mosquitoes within a given population would carry the disease agent that it would require a very large sample size in order to detect its presence. By increasing both the capacity to attract vector mosquitoes, and the number of monitoring traps that can be placed over the same area within the same time and budget constraints, Vectrax could substantially improve the range and sensitivity of current monitoring programs for established and emerging mosquito-borne illnesses, both within the U.S. and abroad. In addition, while no trap design currently available has demonstrated the capacity to reduce mosquito populations or frequency of biting to any significant degree, the increased potency and decreased cost of the Vectrax attractant compared to CO2 could enable a method of population control by mass trapping, by enabling deployment of traps at a high enough density for an effective mass trapping program.

Vectrax can also be blended with a small quantity of insecticide to create an A&K formulation. Broadly-defined, the A&K technique of pest control consists of attracting adult males, females, or both sexes of a pest species to an insect control agent (e.g., insecticide, sterilant, or insect pathogen). The insect attractant can be a chemical attractant, a visual cue, an acoustic cue, or a combination of these. A highly effective attractant and appropriate insecticide are indispensable ingredients of an effective A&K product. For such a formulation to work, insect pests must be lured to a toxicant, which they must contact and/or feed upon. Contact with the toxicant must then either kill the insect or, at minimum, result in sublethal effects that preclude that insect from effectively performing behaviors that are essential to its survival (feeding behavior, escape responses, etc.), or the survival of its population (effective courtship, mating success). The attractant must be at least as effective, if not more so, as attractants naturally present in the environment, so that the A&K formulation successfully out-competes them and lures the insect pest to the control agent. In many cases, the A&K also contains phagostimulants that induce the insect pest to consume the toxicant formulation. One way for A&K formulations to outcompete existing, natural sources of the stimuli in the treated environment, is by having point sources present at significantly higher densities than the competing natural sources, and/or by being significantly more attractive to the target pest.

Though both methods rely on chemical toxicants to suppress pest populations, A&K techniques present many advantages over cover sprays of conventional insecticides. Attract and kill typically deploys smaller amounts of toxicants, often contained within discrete point sources and coupled to a species specific attractant, reducing the likelihood of negative environmental and non-target effects. There are also substantial economic benefits to the use of A&K over blanket pesticide sprays. Various attempts have been made to describe and quantify the negative impacts that pesticides have on environmental and human health [58], accounting for the combined costs of all pesticides for each country, and not only the costs of individual pesticides at a local scale. For example, Leach and Mumford (2008) developed a simple tool that quickly assesses the indirect costs of individual pesticides based on their particular toxicological and environmental behavior, providing a tool to rapidly estimate the environmental and public health impacts of pesticides in U.S. dollars/hectare/application. The model calculates the cost of a cover spray of Malathion 50% EC at $8.72/ha (this is external cost of an application, not the actual cost of the pesticide) while if the same pesticide were applied as an A&K bait, the cost plummets to $0.04 per ha.

Despite these advantages, with few notable exceptions, the use of formulations baited with phytochemical attractants used by mosquitoes and other biting dipterans to locate sugar meals, remains largely unexplored. Very little is known of the composition of the natural volatile plant semiochemical blends attractive to biting dipterans, and few extracts or synthetic blends of these phytochemicals have been developed for use in vector management formulations. Furthermore, current A&K formulations lack rainfastness, and sun/UV protection, and consequently have shorter field lives than desired. Their effectiveness is drastically reduced with the incidence of rain, and they invariably leak or drift, contaminating soils and waterways. Current A&K producers frequently create formulations that lack the species selectivity necessary to allow it to be applied in the field without causing environmental or ecological damage. While A&K may be very selective (i.e., if insect sex pheromones are used as attractants), attractants with broad effects, such as plant kairomones, sugar solutions, food fermentation residues, and their combinations, need to be tested for their impact on non-target organisms.

The present invention addresses all these shortcomings in previous A&K strategies targeted toward biting dipterans. Through an extensive series of lab bioassays and semi-field mesocosm (large mosquito-proof greenhouses) trials, we have successfully developed a number of attractant blends that have proven so highly effective against three major vector genera of mosquitoes, *Anopheles* (vector of malaria, the deadliest MBD of the modern world), *Aedes* (vector of Dengue fever, one of the most prevalent MBDs in tropical regions), and *Culex*, (vector of WNV and other arboviruses), that it out-competes natural plant odors and attractants. We have also developed an irresistible phagostimulant blend of sugars and proteins that causes the mosquito to feed continuously on the formulation until it is fully engorged, even when the formulation contains lethal doses of insecticide.

In addition to this high degree of efficacy as a mosquito attractant and phagostimulant, Vectrax also represents a substantial improvement over other forms of mosquito control in terms of safety, affordability, and long-term sustainability. This formulation is composed entirely of organic ingredients, for maximum safety to humans and the environment. As a thick, gel-like material applied in discrete point sources rather than a spray film that covers all surfaces, this A&K formulation is amenable to targeted, strategic application, allowing the user to select application sites that may be expected to have the largest possible impact on the target (areas of high mosquito populations, key mosquito breeding sites, etc.). This method of application reduces the overall quantity of insecticide required to be applied over a given area to achieve and maintain effective control (due to the powerful attraction and phagostimulation that the formulation exerts on the target pests), while eliminating the risk of spray drift and decreasing the likelihood of contamination of the soil or water where it is applied. Vectrax possesses a particularly valuable advantage over other forms of pesticides in that it has demonstrated no negative impacts on the critical pollinator species, *Apis mellifera*, the honey bee. Vectrax is surprisingly repellent to honey bees and other hymenoptera. Preliminary studies showed that honey bees completely avoided the floral attractant when it was placed in their foraging zones: during 5 minute observations of feeding stations containing 20% sugar solution, we observed an average of 33±5.8 bee visitations. There were zero visitations on feeding stations containing the same 20% sugar solution spiked with a miniscule quantity (0.01%) of our floral attractant.

Vectrax as an A&K solution is a more economically sustainable pest management solution than insecticide cover sprays, as well as a more environmentally friendly one. Aside from requiring a lesser quantity of insecticide to be applied per unit area to achieve effective control, Vectrax can be formulated into a sprayable liquid formulation that will quickly solidify after application, to protect the active ingredients from degradation and extend its field life. This results in a lower frequency of application to maintain mosquito population suppression, reducing the overall cost of the pest control strategy. Furthermore, as an attractant formulation amenable to tank mixing, designed to function in combination with a wide variety of different insecticides, Vectrax is far less susceptible to the development of resistance in the target insects: research has shown that rotation of different insecticides is an effective method of preventing the build-up of resistant pest populations, as the development of resistance to multiple classes of toxins becomes increasingly unlikely. The tank-mixed Vectrax A&K solution can be applied in the field in one of two ways: 1) in relatively large quantities contained within bait stations, which would be particularly useful in areas of high pest population density; and 2) in a large number of much smaller point sources, as applied through manual or mechanical spraying equipment. This manner of application would be of use in areas with lower mosquito population density, as the high density of point sources would dramatically increase the likelihood that the target insects will encounter, respond to, and consume the insecticide-laced formulation.

While this invention was originally developed as an attractant for biting diptera, the floral blend that lends Vectrax its efficacy proved to be extremely complex in chemical composition and behavioral effects, with different compounds eliciting different responses in insects exposed to them. Certain components within this blend have demonstrated a strong repellent effect against New and Old World species of sand flies, opening up a new and unexpected avenue of pest control by means of this invention. Through a series of dual-choice bioassays, a new combination of plant volatile semiochemicals was identified, which acts as a powerful repellent against two vector species of sand flies, *Lutzomyia longipalpis* and *Phlebotomus dubosqui* (vectors of leishmaniasis). This semiochemical blend proved more effective against this species than DEET (N, N-diethyl-meta-toluamide), currently considered the gold standard in insect repellents, even when the latter was applied at a substantially higher application rate (I mg semiochemical blend vs. 1,200 mg DEET), suggesting that our invention has the capacity to repel sand flies more effectively with less material and less cost required than topically applied products like DEET. Female sand flies repelled from host environments will be less likely to obtain a blood meal, reducing egg production, while aggregation by males, which typically occurs near hosts, will also be impeded by the presence of a repellent. Both of these interventions will lead to a decrease in reproductive success within the treated area, and over time, a reduction in sand fly population size.

Regardless of the application method—whether as an attractant for mosquitos or a repellent for sand flies, as an insecticide-free method of pest control or blended with small amounts of reduced-risk toxicants to create a more environmentally sound A&K formulation—this invention will diminish the impacts of biting diptera by a) reducing the frequency of biting events, and consequently, opportunities for vector-borne disease transmission to occur; b) reducing loss of productivity in susceptible livestock due to irritation and blood loss; and c) improve conditions at outdoor work sites, leading to greater worker comfort and productivity. This is highly advantageous in any location where mosquitoes create nuisance and health problems, but is particularly vital in developing areas of the world, where methods of vector-borne pathogen prevention are still largely reliant on indoor interventions (i.e., insecticide-treated bed nets to prevent malaria transmission), leaving outdoor biting events a major source of transmission.

BRIEF SUMMARY

One embodiment of the present disclosure is directed toward a composition for affecting dipteran hematophagous parasites. The composition includes at least one dipteran semiochemical and at least one phagostimulant. In particular, the semiochemical may be a floral attractant and the phagostimulant may be sugar-based. Further, the semiochemical may be a mosquito attractant and/or a sand fly repellant.

The semiochemical and phagostimulant may be contained within a substrate. In particular, examples of, and methods of making, suitable substrates are recited in U.S. Pat. No. 7,887,828 titled Dual Action Organic Formulation to Control Two Stages of Insect Pests, the entirety of which is incorporated by reference herein. The substrate may, for example, be a wax emulsion, microspheres, a latex solution, hot melt glue, a resin, or plastic flakes. In the case where the substrate is a wax emulsion, it may be a wax carrier such as a paraffin wax, carnauba wax, beeswax, candelilla wax, fruit wax, lanolin, shellac wax, bayberry wax, sugar cane wax, microcrystalline wax, ozocerite, ceresin, montan wax, or combinations thereof. In a particular embodiment, the wax emulsion may include 30% by weight paraffin wax; 4% by weight soy oil; 2% by weight sorbitan monostearate; 1% by weight vitamin E; and 58% by weight distilled water. In another embodiment, the wax emulsion may include 45% by weight microcrystalline wax; 6% by weight soy oil; 3% by weight sorbitan monostearate; 1% by weight vitamin E; and 40% by weight distilled water. In yet another embodiment, the substrate may be a hot melt glue. The hot melt glue may be, for example, a polymer of ethylene-vinyl acetate, polyethylene, polypropylene, a polyamide, or a polyester.

In certain embodiments wherein it is intended to kill the dipteran hematophagous parasite, or another insect, the composition may further include a pesticide.

Examples of suitable compositions for use with the present disclosure are recited below in Tables 1 and 2:

TABLE 1

| | |
|---|---|
| linalool | 5%-25% by weight; |
| phenylacetaldehyde | 5%-45% by weight; |
| β-myrcene | 0%-50% by weight; |
| citronella oil | 5%-45% by weight; |
| eucalyptol | 5%-25% by weight; |
| geraniol | 10%-20% by weight; |
| camphene | 5%-30% by weight; |
| ocimene | 1%-45% by weight; |
| anethole | 5%-45% by weight; |
| anisic acid methyl ester | 0%-25% by weight; |
| phenethyl alcohol | 1%-35% by weight; |
| caryophyllene | 2%-20% by weight; |
| 4-methoxybenzyl alcohol | 1%-15% by weight; |
| methyl salicylate | 0.1%-20% by weight; |
| γ-terpinene | 1%-45% by weight; |
| α-terpinene | 1%-45% by weight; |

TABLE 1-continued

| | |
|---|---|
| limonene | 5%-30% by weight; |
| BHT | 1%-25% by weight; |
| dipentene | 1%-15% by weight; |
| sugars | 5%-60% by weight; |
| thickeners | 0.5%-5% by weight; |
| preservatives | 0%-2% by weight; |
| antioxidants | 0.1%-15% by weight; |
| sunlight stabilizer | 0.1%-10% by weight; |
| wax | 2%-40% by weight; |
| emulsifier | 0.5%-5% by weight; |
| soybean oil | 1%-40% by weight; and |
| liquid carrier | 1%-70% by weight. |

TABLE 2

| | |
|---|---|
| linalool | 5%-25% by weight; |
| phenylacetaldehyde | 5%-45% by weight; |
| β-myrcene | 0%-50% by weight; |
| anethole | 5%-45% by weight; |
| anisic acid methyl ester | 0%-25% by weight; |
| phenethyl alcohol | 1%-35% by weight; |
| caryophyllene | 2%-20% by weight; |
| 4-methoxybenzyl alcohol | 1%-25% by weight; |
| methyl salicylate | 0.1%-20% by weight; |
| γ-terpinene | 1%-45% by weight; |
| α-terpinene | 1%-45% by weight; |
| limonene | 5%-30% by weight; and |
| BHT | 1%-25% by weight. |

Another embodiment of the present disclosure is directed toward methods of affecting dipteran hematophagous parasite populations. The method includes administering a composition to a region known or suspected to contain dipteran hematophagous parasites, wherein the composition includes at least one dipteran semiochemical and at least one phagostimulant. The method may be used to attract mosquitoes. The method may be used to monitor the population of dipteran hematophagous parasites and/or to kill them by including a pesticide within or nearby to the composition or by trapping the parasites at the site of the composition. The method may be used additionally, or alternatively, to repel sand flies. One benefit of the methods described herein is that the compositions do not negatively impact honey bee populations within the administered region. Another benefit of the described methods are that the composition may be administered in numerous forms, including but not limited to, sprayable forms, monolithic lures, and sticky trap adhesives.

DETAILED DESCRIPTION

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

The compositions described in the present disclosure, coined Vectrax, are long-term slow release formulations that protect all incorporated active ingredients (the potent attractants, phagostimulants and insecticides) from rain, decomposition and degradation. The dipteran pest control applications for which this formulation may be implemented are many and varied. By incorporating active ingredients (AIs) in such a controlled release matrix, the effectiveness and longevity of these AIs in the field can be significantly improved, to such an extent that a single application can provide weeks to months of protection against the target dipterans. As a result of this extended longevity and field hardiness, Vectrax can be deployed as a preventative measure, ahead of outbreaks of mosquitoes and other target biting dipterans. As a flowable, thick liquid formulation, this product is amenable to mechanical application through standard, readily available spray equipment, but it effectively anchors to the substrate to which it is applied, so that it doesn't dislodge during rain. Once the formulation has solidified, it protects the AIs continuously, so that it sustains consistent and effective AI release over an extended period of time, ensuring full strength attraction, phagostimulation and/or insecticidal effects, depending on the blend of components incorporated.

As floral- and sugar-based bait for mosquitoes, of both vector and nuisance species, so powerfully attractive to mosquitoes that it out-competes natural plant odors and attractants, Vectrax may be applied alone, to substantially improve monitoring efforts for vector mosquitoes of both established and emerging mosquito-borne pathogens in the U.S., by providing a lure that is as attractive or more so than current $CO_2$-baited traps at only a very small fraction of the cost. For example, one trial showed that within a single hour, a single passive trap, baited with a small quantity of variant of the Vectrax lure, captured virtually every mosquito released in test rooms (featureless 5×4×3 m test rooms, temperature controlled at 27±3° C., humidity at 85±7%, lights off). An average of 98±1% (10 replicates) of 500 nulliparous *Aedes aegypti* females were captured within this interval. This result was achieved with the use of a very simple, inexpensive, passive glue trap design: a PVC tube (10.2 cm diameter, 30.5 cm tall) treated with a pressure sensitive glue to capture mosquitoes upon first contact of their tarsi, and thus preserve captured specimens for further identification and analysis. The enhanced monitoring capacity that could be achieved through the application of such a simple trap-lure system could help not only to improve strategic timing and location of mosquito control efforts (i.e., identification of key mosquito reproductive sites and targeting of high populations by insecticide sprays), but also to improve surveillance of mosquito-borne illnesses, both those already established in U.S. populations, such as WNV, and those threatening to invade from foreign regions, like the recent detections of Chikungunya and Dengue fever in the southern states.

Vectrax could also be blended with small quantities of insecticide to create an attract and kill (A&K) formulation that could be applied in strategic locations to draw mosquitoes away from potential hosts, both human and animal, and kill them before they have a chance to bite. Since Vectrax is designed to function primarily with insecticides that work by ingestion (requiring the target insects to actually consume the formulation in order to be effective), the formulation also contains extremely powerful sugar- and protein-based phagostimulants (feeding stimulants), which have been shown to induce target mosquitoes to feed continuously on Vectrax until fully engorged, even when the formulation contains lethal doses of insecticide. In large semi-field trials conducted in the large mesocosms at Ohio State University, a single 100 mL point source of Vectrax, impregnated with 2% permethrin (by weight of emulsion), applied to a single leaf within the mesocosm, successfully attracted and killed roughly half of the 500 virgin two-day-old female *Anopheles gambiae* mosquitoes released the first night after their release, despite the presence of many other plants known to be attractive to sugar-seeking mosquitoes. The remaining half of the released mosquitoes were killed during the second night, eliminating virtually every mosquito in the treated mesocosms within 48 hours. In contrast, more than 90% of the mosquitoes released in the control mesocosms remained alive at the end of the second day following their release.

In addition to this exceptional level of efficacy, careful design of the attractant and phagostimulant AIs, as well the various components of the controlled release emulsion, has resulted in a product that can be tank mixed with a broad range of registered pesticides, ensuring that Vectrax will be adoptable in virtually any location, regardless of what toxicants are most effective against a given species in a given environment or situation. This adaptability also presents a considerable advantage in terms of long-term applicability: because Vectrax can function effectively as an A&K system with so many different types of insecticides, it is nearly invulnerable to the development of resistance in the target insects. It is also a more sustainable method for the control of dipteran pests than traditional insecticide cover sprays. Vectrax is composed entirely of organic ingredients, for maximum safety to humans and the environment, even when toxicants are incorporated. By selecting only reduced-risk insecticides, those that work as stomach poisons rather than simply by contact, chances are lessened that non-target species will be harmed: only insects that are attracted to the Vectrax point source and actually feed upon the material will suffer negative effects. Of particular importance and value is Vectrax's lack of negative effects on honey bee (*Apis mellifera*) populations, especially given the severe and still largely unexplained decline in honey bee populations around the world. Vectrax is surprisingly repellent to honey bees and other Hymenoptera. Preliminary studies showed that honey bees completely avoided the floral attractant when it was placed in their foraging zones: during 5-minute observations of feeding stations containing 20% sugar solution, an average of 33±5.8 bee visitations was observed. There were no visitations to feeding stations containing the same 20% sugar solution spiked with 0.01% of our floral attractant. Finally, Vectrax will be designed to reduce the exposure of the pesticide in the environment by retaining, protecting and slowly releasing the AI from discreet Vectrax point sources (instead of the blanket cover sprays used for conventional insecticides). These point sources become beacons for the target species, and are easily avoidable by non-targets. Alternatively, larger quantities of Vectrax can be deposited in bait stations, which would be particularly useful in areas of high pest population density.

Vectrax can also be deployed as a vehicle for the controlled release of repellent plant volatiles, to manage sand fly populations. Although originally evaluated as a sand fly attractant, as it was for mosquitoes, ISCA Technology scientists discovered a number of volatile plant-derived compounds that have demonstrated an extremely high degree of repellency against both New and Old World sand flies, using only miniscule AI quantities, and in lab tests it has been observed to exert a "halo effect" of repellency not seen in topically applied products. In a series of dual-choice bioassays, in which two leishmaniasis vectors, *Lutzomyia longipalpis* and *Phlebotomus dubosqui*, were given a choice between a chamber treated with a variant of Vectrax and a control chamber, both species overwhelmingly chose the control (95% *L. longipalpis*; 100% *P. dubosqui*), demonstrating strong repellency. In comparison, the same experiment conducted with N, N-diethyl-meta-toluamide (DEET), considered the gold standard in insect repellents, demonstrated weaker repellency to *P. dubosqui* than Vectrax—only 79% flies selected the untreated over the treated chamber, despite a higher application rate (1,200 mg DEET vs. 1 mg Vectrax). This plant-based repellent formulation could reduce sand fly populations in a number of ways. Female sand flies repelled from host environments by Vectrax will be less likely to obtain a blood meal, reducing egg production, while lek formation by males, which typically occurs near hosts, will also be impeded by the presence of a repellent. Both of these interventions will lead to a decrease in reproductive success within the treated area, and over time, a reduction in sand fly population size. The volatile nature of this blend suggests that when incorporated into a controlled-release formulation, it will act over greater distances than current repellent formulations (e.g. DEET)—and is therefore capable of protecting an entire area from sand flies, rather than a single individual—and will remain active for longer periods.

Vectrax formulations belong to a "matrix-type" or "monolithic" category of controlled-release devices. These monolithic dispensers are defined as devices where the active ingredient (AI) is dispersed or dissolved in a polymer matrix. Release of the AI from a monolithic device occurs by diffusion and can be described macroscopically by Fick's Law, which states that the movement of a molecule by diffusion is directly proportional to the concentration of that molecule in a system. Microscopically, if one follows the movement of a molecule of an active agent through a matrix, this molecule begins its journey in one of two ways. If it is dispersed in the matrix, it begins its journey by dissociating from other molecules in its crystal cell and solubilizing into the polymer phase. If it is dissolved in the matrix, then this step is bypassed. The molecule then diffuses through amorphous regions in the matrix that comprise the free volume of the system. The molecule can move through the matrix in one of two ways. If it is very small compared to the size of the amorphous spaces in the matrix, then it will diffuse through the matrix by moving from one such space to another. If it is very large compared to the size of those spaces, then segments of the polymer comprising the matrix will have to be rearranged for diffusion of the active agent molecule to occur. Crystalline regions in the matrix are virtually impermeable to molecules of the active agent. Upon reaching the surface of the matrix, it will be released into the environment. A series of factors influence the rate of release of an active agent from a monolithic device and include properties of the matrix material as well as properties of the active agent. The temperature of the matrix influences release of the active agent; at higher temperatures the free volume is increased, and diffusion occurs faster. At lower temperatures, the free volume is decreased, and diffusion is slower. The thermal history of a polymer can also increase or decrease the free volume of the system and lead to changes in the diffusional rate of an active agent. The property of the AI having the greatest influence on its release rate is its molecular weight. Generally, larger molecules take more time to make their way through the free space of a matrix. The partition coefficient of the active agent between the matrix and the environment can also influence the release rate of that agent. If the agent readily partitions to the environment, then its rate of release will be diffusion-controlled and first order. If, however, partitioning of the active agent to the environment is relatively slow, then its partition coefficient will determine its release rate from the matrix, and the device will exhibit zero-order release kinetics. The partitioning of the AI to the environment is a function of its solubility in the matrix; compounds more soluble in the matrix partition to the environment more slowly. Vectrax emulsions in a field environment exhibit diffusion-controlled release. The surface area of the device also influences its release rate. Vectrax dispensers with larger surface areas release AIs at faster rates. The release rate of a Vectrax formulation containing a fixed amount of semiochemical can be modulated simply by changing a few parameters of the formulation, which include the type of components used (e.g., wax composition, emulsifiers), their proportion in the formulation (e.g., percentage of water, oil or wax), the stage in manufacturing when different components are added, rheology, and finally, the characteristics of the dispenser upon application in the field (e.g., applied as microdollops of 1-10 μg each or larger dollops of 1-5 g each).

Application Methods for the Invention:

Vectrax for Mosquitoes.

Vectrax can be deployed to manage nuisance and vector mosquito populations in outdoor environments in three ways: 1) for monitoring purposes, when applied as a lure in virtually any form of trap; 2) in self-contained bait stations, either as an attractant alone, to draw the insects away from important or vulnerable areas, or in combination with an insecticide to attract and kill them, permanently removing them from the environment; and 3) as a sprayable A&K formulation that can be applied manually or through a wide variety of mechanized equipment, directly to foliage within the mosquitoes' habitat. Though this formulation highly flexible in terms of application rate and method, a guideline application procedure for each method described above is included below.

Monitoring.

Vectrax (attractant only) may be applied as a lure either by itself, or as a complement to any other type of attractant, including $CO_2$, in virtually any type of trap. To use the formulation in this way, a small quantity of Vectrax, shaken or stirred to ensure that all incorporated AIs are in suspension, is deposited onto a stable substrate, such as a cotton ball or a segment of cotton gauze, and then secured within the trap, typically through the application of some form of adhesive. The applied point source may range in size from a few μg to 10 s of grams in size, depending on a) the concentration/dilution of the attractant, and b) how long the attractant is desired to maintain its activity in the field. Alternatively, a quantity of the Vectrax attractant could be blended directly into the adhesive itself, before being applied within the trap. Blending may be accomplished through a wide variety of manual or mechanized mixing equipment. Vectrax-baited traps may be deployed at single locations, in order to lure mosquitoes away from sensitive areas (i.e., rural residences, backyards, recreational activity sites) and remove them from the environment by trapping them, or as part of a mosquito management strategy, placed at whatever locations and whatever density is thought to be required to effectively suppress mosquito populations.

Vectrax Ball Stations.

To apply Vectrax within bait stations, the formulation—again, previously shaken or stirred—is loaded into a reservoir that provides the target insects with easy access to the attractant material, similar to a hummingbird feeder. The attractant formulation may be applied by itself or blended with a small quantity of an appropriate insecticide (the insecticide cyazypyr has proven quite effective in laboratory and mesocosm trials). In order to maintain maximum A&K efficiency, the toxicant component should be blended into the Vectrax attractant formulation as close to the time of application as possible. The attractant or A&K formulation may be loaded into the bait station in amounts ranging from a few grams to several liters, depending on the desired field life. If desired, a sponge or other absorbent material may be applied with the formulation, to facilitate landing by the mosquitoes. As with Vectrax-baited traps, Vectrax bait stations may be deployed singly, as a means to divert or attract and kill mosquitoes in sensitive environments (i.e., rural residences, backyards, recreational activity sites), or as part of a mosquito management strategy, placed at whatever locations and whatever density is thought to be required.

Sprayable A&K.

As with a Vectrax A&K formulation deployed in bait stations, a formulation intended to be applied directly to foliage as a liquid material should be blended with its toxicant component immediately prior to its application. Once the formulation is thoroughly blended, it may be applied by hand, using simple tools such as knives, spatulas, brushes, or syringes; or mechanically, using anything from a backpack sprayer to a tractor or aerial spray equipment. The rate and quantity at which the formulation should be applied will depend on the needs of the specific pest management situation, such as the desired field longevity (larger point sources will maintain their activity for a longer period than smaller point sources) and the density of the pest population at the site, but for many studies examining Vectrax as an A&K product, an application rate of 1 liter per hectare has proven adequate.

Vectrax for Sand Flies.

To apply Vectrax as a spatial and contact repellent for New or Old World sandflies, the formulation may be applied in an identical manner as for bait stations for mosquitoes or sprayable liquid formulation (see above) though in this case, these measures will serve the opposite purpose of repelling the target pest away from treated sites, rather than drawing the insects to them for removal or monitoring. Because of this dual activity, in areas treated with the Vectrax sand fly repellent where mosquitoes are also present, a small amount of insecticide active against biting Diptera can be blended with the formulation prior to application. Once the formulation has been properly blended, it may be applied near sensitive sites, such as the outdoor area surrounding a home, outdoor worksites known to be heavily infested with sand flies, or key sand fly reproductive sites. When deploying the repellent in a self-contained repellent station, the amount of formulation to be applied may range from a few grams to several liters, as with mosquito bait stations, depending on the desired field longevity. When applying as a spray over larger areas, application rates/quantities are similarly flexible, but an application rate of 1 kg per acre has proven effective in most previous tests.

Experimental Results Containing Insecticide:

Materials:

Two formulations 250 mls each were prepared: i) Control formulation containing blank vectrax, and ii) Treatment formulation containing vectrax+insecticide (permethrin). Cotton wool. Thatching materials (bamboo leaves). Plastic sheet.

Procedure:

One hour before the release of mosquitoes, i) a plastic sheet was laid on the roof of each respective control and treatment Hut, ii) Thatching materials were fixed on top of the plastic sheet for both huts in control and treatment spheres (the plastic sheet was to prevent contaminations of original thatching materials of the huts), and iii) Then cotton wool soaked in the blank vectrax for control sphere and vectrax+insecticide for the treatment sphere were placed on paper cups turned upside down to six stations of this kind in both spheres Mosquitoes Release:

At 10 AM on the day of release, 1 to 2 days old female *An. gambiae* ss were separated at equal numbers in the cages and starved until the time of release (1 to 2 days old because at that age sugar is the preferred meal). At eight hours of starvation, the mosquitoes were released in both spheres at an equal number. The release was made by placing the cage at one corner of the sphere and providing a small exit from the cage (approximately 15 cm). Then mosquitoes were left in hut for 24 hrs so that they could acclimatize with the Vectrax control or Treatment Vectrax. After 24 hrs, a human subject went in the respective nets in huts and counted the number of mosquitoes coming to bite. The recapturing went on for three days following the release. Scores were then recorded and totaled.

The above description is given by way of example, and not limitation. Given the above disclosure, one skilled in the art could devise variations that are within the scope and spirit of the invention disclosed herein, including the use of various semiochemicals and pesticides to achieve the same intended effect. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A composition for attracting, repelling, and/or disrupting the mating of dipteran hematophagous parasites comprising:

| | |
|---|---|
| linalool | 5%-25% by weight; |
| phenylacetaldehyde | 5%-45% by weight; |
| β-myrcene | 0%-50% by weight; |
| citronella oil | 5%-45% by weight; |
| eucalyptol | 5%-25% by weight; |
| geraniol | 10%-20% by weight; |
| camphene | 5%-30% by weight; |
| ocimene | 1%-45% by weight; |
| anethole | 5%-45% by weight; |
| anisic acid methyl ester | 0%-25% by weight; |
| phenethyl alcohol | 1%-35% by weight; |
| caryophyllene | 2%-20% by weight; |
| 4-methoxybenzyl alcohol | 1%-15% by weight; |
| methyl salicylate | 0.1%-20% by weight; |
| γ-terpinene | 1%-45% by weight; |
| α-terpinene | 1%-45% by weight; |
| limonene | 5%-30% by weight; |
| BHT | 1%-25% by weight; |
| dipentene | 1%-15% by weight; |
| sugars | 5%-60% by weight; |
| thickeners | 0.5%-5% by weight; |
| preservatives | 0%-2% by weight; |
| antioxidants | 0.1%-15% by weight; |
| sunlight stabilizer | 0.1%-10% by weight; |
| wax | 2%-40% by weight; |
| emulsifier | 0.5%-5% by weight; |
| soybean oil | 1%-40% by weight; and |
| liquid carrier | 1%-70% by weight. |

2. The composition of claim 1, wherein the composition semiochemical is a mosquito attractant.

3. The composition of claim 1, wherein the composition semiochemical is a sand fly repellant.

4. The composition of claim 1, wherein the wax is selected from the group consisting of paraffin wax, carnauba wax, beeswax, candelilla wax, fruit wax, lanolin, shellac wax, bayberry wax, sugar cane wax, microcrystalline wax, ozocerite, ceresin, montan wax, and combinations thereof.

5. The composition of claim 1, wherein the composition comprises:
30% by weight paraffin wax;
4% by weight soy oil;
2% by weight sorbitan monostearate;
1% by weight vitamin E; and
58% by weight distilled water.

6. The composition of claim 1, wherein the composition comprises:
45% by weight microcrystalline wax;
6% by weight soy oil;
3% by weight sorbitan monostearate;
1% by weight vitamin E; and
40% by weight distilled water.

7. The composition of claim 1 further comprising a pesticide.

8. A composition for attracting, repelling, and/or disrupting the mating of dipteran hematophagous parasites comprising:

| | |
|---|---|
| linalool | 5%-25% by weight; |
| phenylacetaldehyde | 5%-45% by weight; |
| β-myrcene | 0%-50% by weight; |
| anethole | 5%-45% by weight; |
| anisic acid methyl ester | 0%-25% by weight; |
| phenethyl alcohol | 1%-35% by weight; |
| caryophyllene | 2%-20% by weight; |
| 4-methoxybenzyl alcohol | 1%-25% by weight; |
| methyl salicylate | 0.1%-20% by weight; |
| γ-terpinene | 1%-45% by weight; |
| α-terpinene | 1%-45% by weight; |
| limonene | 5%-30% by weight; and |
| BHT | 1%-25% by weight. |

9. The composition of claim 8, further comprising a phagostimulant.

10. The composition of claim 9, wherein the phagostimulant is sugar-based.

11. The composition of claim 9, further comprising a substrate.

12. The composition of claim 11, wherein the substrate is selected from the group consisting of a wax emulsion, microspheres, a latex solution, hot melt glue, a resin, and plastic flakes.

13. The composition of claim 12, wherein the substrate is a hot melt glue comprised of a polymer selected from the group consisting of ethylene-vinyl acetate, polyethylene, polypropylene, a polyamide, or a polyester.

14. The composition of claim 8 further comprising a pesticide.

15. A method of attracting, repelling, and/or disrupting the mating of dipteran hematophagous parasite populations comprising:
administering a composition to a region known or suspected to contain dipteran hematophagous parasites, the composition comprising:

| | |
|---|---|
| linalool | 5%-25% by weight; |
| phenylacetaldehyde | 5%-45% by weight; |
| β-myrcene | 0%-50% by weight; |
| anethole | 5%-45% by weight; |
| anisic acid methyl ester | 0%-25% by weight; |
| phenethyl alcohol | 1%-35% by weight; |
| caryophyllene | 2%-20% by weight; |
| 4-methoxybenzyl alcohol | 1%-25% by weight; |
| methyl salicylate | 0.1%-20% by weight; |

-continued

| | |
|---|---|
| γ-terpinene | 1%-45% by weight; |
| α-terpinene | 1%-45% by weight; |
| limonene | 5%-30% by weight; and |
| BHT | 1%-25% by weight. |

16. The method of claim 15, wherein the composition attracts mosquitoes.

17. The method of claim 16, further comprising the step of monitoring the population of dipteran hematophagous parasites.

18. The method of claim 16, wherein the composition further comprises a pesticide.

19. The method of claim 16, wherein the composition repels sand flies.

20. The method of claim 15, wherein the composition does not negatively impact honey bee populations.

21. The method of claim 15, wherein the composition is administered in a form selected from the group consisting of a sprayable form, a monolithic lure, and a sticky trap adhesive.

* * * * *